United States Patent [19]
Boehm

[11] Patent Number: 5,508,456
[45] Date of Patent: Apr. 16, 1996

[54] 9-CIS TRITIUM-LABELED RETINOIDS AND INTERMEDIATES, METHODS FOR THEIR SYNTHESIS AND METHODS FOR THEIR USE IN DISCOVERING RETINOID X RECEPTOR LIGANDS

[75] Inventor: Marcus F. Boehm, San Diego, Calif.

[73] Assignee: Ligand Pharmaceuticals Incorporated, San Diego, Calif.

[21] Appl. No.: 250,373

[22] Filed: May 27, 1994

Related U.S. Application Data

[63] Continuation-in-part of Ser. No. 100,705, Jul. 30, 1993, abandoned.

[51] Int. Cl.[6] .................................................. C11C 3/00
[52] U.S. Cl. .................... 554/163; 554/124; 554/132; 554/154; 554/221; 554/224; 252/625
[58] Field of Search .................................. 554/124, 132, 554/154, 163, 221, 224; 424/111; 252/625

[56] References Cited

U.S. PATENT DOCUMENTS

| | | | |
|---|---|---|---|
| 4,171,318 | 10/1979 | Chan et al. | 200/404 |
| 4,880,941 | 11/1989 | Shroot et al. | 549/57 |
| 5,073,361 | 12/1991 | Shroot et al. | 424/1.1 |
| 5,149,631 | 9/1992 | Shroot et al. | 435/7.24 |
| 5,196,577 | 3/1993 | Shroot et al. | 562/490 |

FOREIGN PATENT DOCUMENTS 3142975 10/1981 Germany.

OTHER PUBLICATIONS

Kaegi et al, Journ of Labelled Cpds & Radiopharmaceuticals vol 17, #8, pp. 1099–1105, 1981.
Chien et al, Journ of Labelled Cpds & Radiopharmaceuticals, vol 16, #5, pp. 791–796, 1979.
Kaegi, H. and J. DeGraw, "Preparation of All Trans–Retinyl–11–[3]H Acetate," 18 *Journal of Labelled Compounds and Radiopharmaceuticals* 1099 (1981).
Chien, P.; Sung, M.; and Bailey, D., "Synthesis of trans–[11–[3]H]–Retinoic Acid and Its 5,6–Epoxide," 17 *Journal of Labelled Compounds and Radiopharmaceuticals*, 759 (1980).
Chien, P. and Sung, M., "Synthesis of 13–cis–(11–[3]H)–Retinoic Acid," 16 *Journal of Labelled Compounds and Radiopharmaceuticals*, 791 (1979).
Andres, H.; Morimoto, H.; and Williams, P., "Preparation and Use of LiEt$_3$BT and LiAlT$_4$ at Maximum Specific Activity," 8 *J. Chem. Soc.* 627 (1990).
Rhee, S., DeGraw, J., and Kaegi, H., "Synthesis of a New Class of Retinoid, [3]H–Labeled TTNPB,[1] with a High Specific Activity," 22 *Journal of Labelled Compounds and Radiopharmaceuticals*, 843 (1985).
Dawson, M.; Hobbs, P., Cameron, J.; and Rhee, S., "Preparation of 9–cis–Retinoic Acid [11,12–[3]H(N)] by Photochemical Isomerization," 33 *Journal of Labelled Compounds and Radiopharmaceuticals*, 245 (1993).
Cainelli, G.; Cardillo, Guiliana; and Orena, Mario, "Synthesis of Compounds Containing the Isoprene Unit; a Stereospecific Synthesis of β–Ionilideneacetic Acid and Dehydro-β–ionilideneacetic Acid, a Key Intermediate to Abscisic Acid," J.C.S. Perkin I, 1579 (1979).
Boehm, M.; McClurg, M.; Pathirana, C.; Mangelsdorf, D.; White, S.; Hebert, J.; Winn, D.; Goldman, M.; and Heyman, R, "Synthesis of High Specific Activity [$^3$H]–9–cis–Retinoic Acid and Its Application for Identifying Retinoids with Unusual Binding Properties," 37 *Journal of Medicinal Chemistry* 3, (1994).

*Primary Examiner*—José G. Dees
*Assistant Examiner*—Deborah D. Carr

[57] ABSTRACT

Methods for the synthesis of 9-cis monotritium-labeled retinoids, and their use in the discovery of Retinoid X Receptor ligands are provided. In addition, 9-cis monotritium-labeled retinoids, as well as novel intermediates and tritium-labeled intermediates formed during the synthesis of 9-cis monotritium-labeled retinoids are also provided.

8 Claims, 1 Drawing Sheet

9-CIS TRITIUM-LABELED RETINOIDS AND INTERMEDIATES, METHODS FOR THEIR SYNTHESIS AND METHODS FOR THEIR USE IN DISCOVERING RETINOID X RECEPTOR LIGANDS

This is a continuation-in-part of application Ser. No. 08/100,705 filed on Jul. 30, 1993, now abandoned.

FIELD OF THE INVENTION

The present invention relates to the synthesis of radiolabeled compounds, and in particular to the synthesis of radiolabeled retinoids and their intermediates. The present invention also relates to the use of radiolabeled retinoids and related compounds in methods to discover retinoid receptor ligands.

BACKGROUND OF THE INVENTION

The role of retinoids such as all-trans retinoic acid (ATRA), 13-cis retinoic acid (13-cis RA) and synthetic retinoic acid (RA) analogs in mediating cell growth and differentiation has generated interest in their pharmacological utility for controlling the treatment of dermatological diseases, such as psoriasis and acne, as well as oncological applications such as chemotherapy and chemoprevention. Significant advances in elucidating the molecular basis of retinoid action now offer the potential for designing RA compounds with improved therapeutic indices.

To date, several receptors for retinoic acid have been identified. These receptors are members of a superfamily of intracellular receptors which function as ligand dependent transcription factors. At present, these receptors have been classified into two subfamilies, the retinoic acid receptors (RARs) and retinoid X receptors (RXRs). The classification of these subfamilies is based primarily on differences in amino acid structure, responsiveness to different naturally occurring and synthetic retinoids, and ability to modulate expression of different target genes. Each RAR and RXR subfamily has three distinct isoforms designated RARα, RARβ and RARγ, and RXRα, RXRβ and RXRγ. The discovery of multiple retinoid receptors raises questions of the functional properties of the distinct subfamilies and their isoforms.

Recently, it has been discovered that 9-cis RA is capable of binding to and modulating gene expression via the RARs and RXRs. Heyman et al., *Cell,* 68:397 (1992). The discovery of this property of 9-cis RA has led to further investigation into the biochemical properties of the RARs and RXRs with naturally occurring RA as well as with synthetic retinoids.

One technique for determining the affinity of RA and synthetic retinoids to RARs and associated proteins is to employ a competitive ligand binding assay using radiolabeled compounds showing RAR activity. See e.g., U.S. Pat. No. 5,196,577. These ligand binding studies require substantial quantities, i.e. greater than 50 milliCuries, of a high specific activity radiolabeled compound (e.g., over 10 Ci/mmol). However, conventional syntheses of radiolabeled retinoids, such as radio-labeled ATRA, using e.g. photoisomerization, is costly and generally cannot yield sufficient quantities of a high specific activity radiolabeled retinoid to effectively conduct ligand binding studies. For example, in H. H. Kaegi et al., *J. Labelled Compd. Radiopharm.,* 18:1099 (1981), reduction of an aldehyde compound with a mixture of lithium borohyride and lithium borotride yielded a of mixture monohyride and monotride intermediates, which were ultimately synthesized to labeled all-trans retinoic acid and all-trans retinyl acetate with an activity of generally less than 3 Ci/mmol. See also, M. I. Dawson et al., *J. Labelled Compd. Radiopharm.,* 33:245 (1993) (photoizomerization to yield μCi quanties of tritium-labeled 9-cis retinoic acid). Thus, conventional syntheses simply cannot provide sufficient quantities of high activity radiolabeled retinoid stereoisomers, such as 9-cis RA and 9,13-dicis RA. Furthermore, to date, no radiolabeled compounds have been identified that show activity on RXRs, as well as RARs.

The entire disclosures of the publications and references referred to above and hereinafter in this specification are incorporated herein by reference.

SUMMARY OF THE INVENTION

The present invention provides methods for the synthesis of 9-cis monotritium-labeled retinoid stereoisomers displaying high specific activity. In a preferred aspect, the methods of the present invention provide for the synthesis of monotritium-labeled 9-cis RA having a specific activity of at least 15 Ci/mmol, more preferably, at least 25 Ci/mmol.

The advantage of monotritium-labeled 9-cis RA over other labeled retinoids is that it binds to all the known RARs and RXRs with approximately equal nanomolar affinities and hence, is a useful probe for determining binding of synthetic retinoids at each of these receptors. Thus, the present invention also provides methods for discovering RXR active and RAR and RXR selective compounds using radiolabeled retinoids in competitive ligand binding assays. In particular, monotritium-labeled 9-cis RA can be used to discover novel ligands which show RXR activity and selectivity.

In particular, the present invention provides a method of producing 9-cis monotritium-labeled retinoids comprising (a) reducing an alkyl ester with a substantially carrier-free metallo tritide to form a ditritium alcohol, (b) oxidizing the ditritium alcohol to a monotritium aldehyde in the presence of an oxidizing agent, (c) condensing the monotritum aldehyde with a carbanion equivalent formed by the addition of a base to a phosphonate or phosphine salt to form a reaction product comprising a mixture of 9-cis monotritium-labeled retinoid ester (e.g., retinoates) stereoisomers, wherein the 11–12 and 13–14 olefin bonds are in either the cis or trans configuration. Further, the reaction product can be hydrolyzed with an aqueous methanolic hydroxide to form a mixture of 9-cis monotritium-labeled retinoic acid stereoisomers, followed by purification and isolation of the individual 9-cis monotritium-labeled retinoid stereoisomers.

In addition, the present invention provides a method for producing a ditritium-labeled olefin comprising reducing an alkyl ester with a metallo tritide to form a ditritium-labeled alcohol, wherein the 9–10 olefin bond is the cis configuration.

The present invention also provides novel intermediates and tritium-labeled intermediates formed during the synthesis of the 9-cis monotritium-labeled retinoid stereoisomers described above.

The present invention further provides methods of identifying retinoid X receptor ligands comprising incubating a radiolabeled compound capable of binding to a retinoid X receptor in a medium containing the retinoid X receptor and a ligand, and comparing the degree to which the ligand binds to the retinoid X receptor in competition with the radiolabeled compound relative to the degree to which the radiolabeled compound binds to the retinoid X receptor in the absence of the ligand. Further, when the radiolabeled compound is active on both retinoic acid receptors and retinoid X receptors (e.g. monotritium-labeled 9-cis retinoic acid), then the methods can be used to identify both retinoid X receptor and retinoic acid receptor specific ligands.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

BRIEF DESCRIPTION OF THE DRAWINGS

The invention may be further illustrated by reference to the accompanying Drawings wherein.

DETAILED DESCRIPTION OF EMBODIMENTS OF THE INVENTION

Figure 1A:
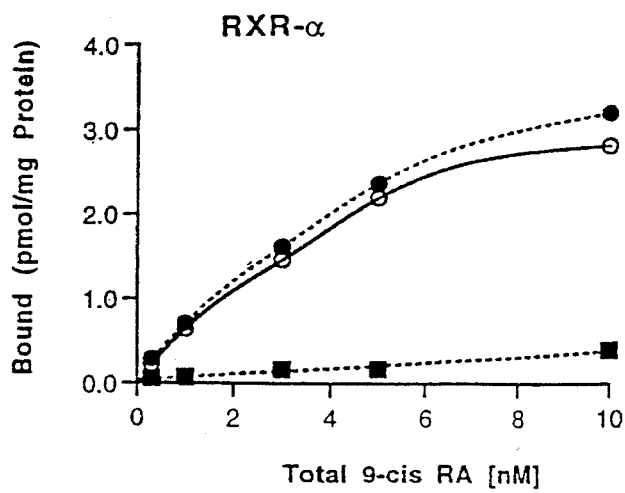
FIG. 1A is a graph showing the total binding ●, nonspecific binding ■, and total specific binding ○ of monotritium-labeled 9-cis retinoic acid ( 11-[$^3$H]-9-cis retinoic acid) to RXRα at increasing concentrations of 9-cis retinoic acid.

In accordance with a first aspect of the present invention, we have developed methods to synthesize 9-cis monotritium-labeled retinoids, the end result of which is a mixture of high specific activity, 9-cis monotritium-labeled retinoid stereoisomers, that can then be isolated to give individual isomerically pure 9-cis monotritium-labeled retinoid stereoisomers. The general sequence of steps for these methods are shown below.

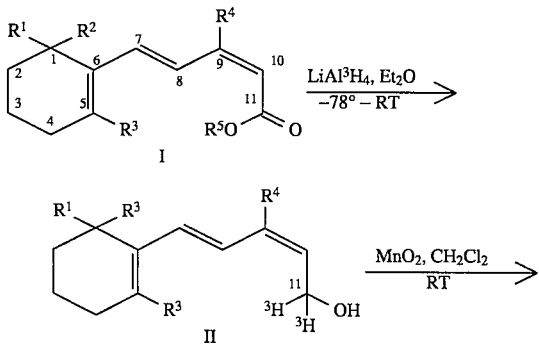

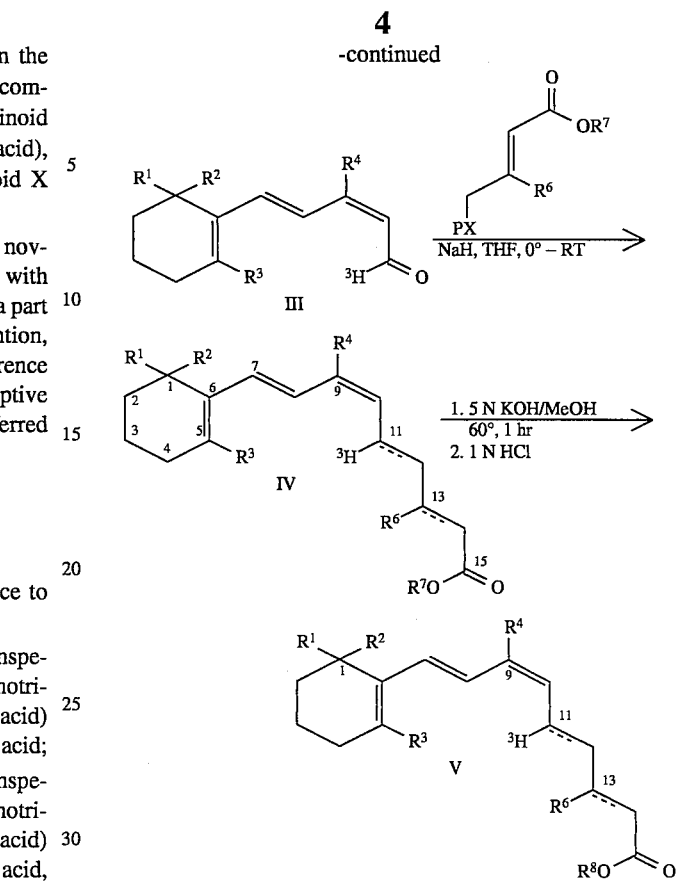

In the above process sequence, $R^1$, $R^2$ and $R^3$ each independently represent hydrogen or a lower straight chain or branched alkyl having 1–6 carbon atoms;

$R^4$ represents hydrogen or a lower straight chain or branched alkyl having 1–12 carbon atoms;

$R^5$ represents a lower alkyl having 1–5 carbon atoms;

$R^6$ represents hydrogen or a lower straight chain or branched alkyl having 1–12 carbon atoms;

$R^7$ represents a lower alkyl having 1–5 carbon atoms;

$R^8$ represents hydrogen or a pharmaceutically acceptable salt;

PX represents dialkyl phosphonate or a triphenyl phosphine salt; and the dashed lines in the structures between carbons 11–12 and 13–14 depict olefin bonds that can be in either the trans or cis configuration.

As used in this disclosure, pharmaceutically acceptable salts include, but are not limited to, pyridine, ammonium, piperazine, diethylamine, nicotinamide, formic, urea, sodium, potassium, calcium, magnesium, zinc, lithium, methylamino, triethylamino, dimethylamino, and tris(hydoxymethyl)aminomethane. Additional pharmaceutically acceptable salts are known to those skilled in the art.

It will be understood by those skilled in the art that certain modifications can be made to the above-described methods that remain within the scope to the present invention. For example, the alkyl ester of I could be directly reduced to the aldehyde III in combination with a substantially carrier-free metallo tritide (e.g. Diisobutylaluminum tritide (DIBAL-$^3$H)), thereby bypassing oxidation step II. Alternatively, an aldehyde could be substituted for the alkyl ester of I, wherein hydrogen is substituted for the $R^5$O group of I. Such an aldehyde in combination with a substantially carrier-free metallo tritide (e.g. LiAl³H₄) could then be reduced, followed by oxidation to the aldehyde of III.

Furthermore, it will also be understood by those skilled in the art that the synthesis of the present invention can have broader application beyond the synthesis of the 9-cis monotritium-labeled retinoids shown above. For example, in place of the alkylester of I, a tetramethyl dehydronaphthyl alkyesters of the formula:

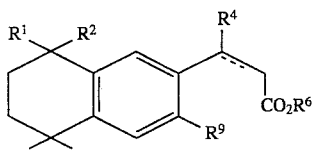

(wherein $R^1$, $R^2$, $R^4$ and $R^6$ each have the same meanings as previously described herein, $R^9$ represents hydrogen, a lower straight chain or branched alkyl having 1–8 carbon atoms, halogen or $OR^{10}$, $R^{10}$ represents hydrogen or a lower straight chain or branched alkyl having 1–8 carbon atoms, and wherein the dashed lines in the structure depict 9–10 olefin bond that can be in either the trans or cis configuration) could be substituted and reduced using the method of the present invention to yield novel ditritium-labeled olefin compounds. Preferably, such ditritium-labeled olefins are formed with the 9–10 olefin bond in the cis configuration.

It will also be understood, that while the process and compounds of the present invention have been illustrated with a tritium label, that deuterium could also be employed to provide isotopically labeled materials which are useful for mass spectral metabolism studies regarding the oxidative metabolites of such labeled compounds, and their corresponding non-labeled versions.

The process sequence of the present invention begins with the reduction of an alkyl ester I, such as methyl (2Z,4E)-3-methyl-5-(2,6,6-trimethylcyclohex-1 -enyl)penta-2,4-dienoate, in combination with a substantially carrier-free metallo tritide, such as lithium aluminum tritide (LiAl³H₄). As used herein, "substantially carrier-free metallo tritide" refers to a radioactive metallo reducing agent comprising all, or essentially all, tritide atoms, with essentially no hydride (hydrogen) atoms. Importantly, this step reduces the alkyl ester I to the alcohol II, which yields essentially pure (i.e., essentially 100%) labeled alcohol II with two tritium atoms at carbon 11. In addition to substantially carrier-free lithium aluminum tritide, which is preferred, another nonlimiting example of a metallo tritide useful in the method of the present invention is substantially carrier-free lithium triethyl aluminum tritide (LiEt₃Al³H).

The second step consists of oxidation of the alcohol II to an aldehyde which is necessary for chain extension. The oxidation can be accomplished using a wide variety of techniques and reagents well known to those skilled in the art to yield the aldehyde III. The oxidation illustrated above is achieved using manganese dioxide (MnO₂) as an oxidizing agent. Other nonlimiting examples of oxidizing agents and procedures useful in the method of the present invention include pyridinium chlorodichromate, pyridinium dichromate, Swern oxidation, and Dess-Martin oxidation.

The third step of this sequence involves condensation of aldehyde III with a carbanion equivalent formed by the addition of a base (NaH) to a phosphonate, such as diethyl 3-ethoxycarbonyl-2-methylprop-2-enyl phosphoate, or a phosphine salt (e.g. triphenyl phosphine) to yield retinoate (retinoid ester) IV. After condensation, a mixture of at least two major isomers and two minor isomers (<20 % of the total) of retinoates IV is observed. Nonlimiting examples of bases useful in the method of the present invention include sodium hydride (NaH), potassium hydride (KH), n-butyl lithium (n-BuLi), s-butyl lithium (s-BuLi), t-butyl lithium (t-BuLi), and sodium amide (NaNH₂).

The fourth and final step in the process involves the hydrolysis of retinoates IV with aqueous methanolic hydroxide (MeOH/KOH) to give 9-cis monotritium-labeled retinoic acid isomers V. Examples of monotritium-labeled retinoid isomers V include, without limitation, 11-[³H]-9-cis retinoic acid and 11-[³H] -9, 13 dicis retinoic acid. After hydrolysis, a desired isomer V can be selectively crystallized from the aqueous methanolic hydroxide solution, or alternatively purified by semi preparative reverse-phase (ODS) high performance liquid chromatography (HPLC). Using the methods described above, monotritium-labeled 9-cis retinoid isomers V are obtained that preferably display a specific activity of at least 15 curies per millimole (Ci/mmol), and more preferably display a specific activity of at least 25 Ci/mmol. Nonlimiting examples of preferred monotritium-labeled 9-cis retinoids made according to the methods of the present invention include (2E,4E,6Z,8E)-5-[³H]-3,7 -dimethyl-9-(2,6,6-trimethylcyclohexen-1-yl)nona-2,4,6,8-tetraenoic acid and (2Z,4E,6Z, 8E)-5-[³H]-3,7-dimethyl-9-(2, 6,6-trimethylcyclohexen-1-yl)nona- 2,4,6,8 -tetraenoic acid.

The synthesis methods of the present invention provide a number of advantages over previously know methods of forming labeled retinoids and related compounds. Importantly, the methods of the present invention provide tritium-labeled 9-cis retinoids, such as monotritium-labeled 9-cis retinoic acid, which are capable of binding with, and modulating gene expression from, both RARs and RXRs. Further, the particular reagents and steps employed in the methods provide high yields, i.e. 100 millicuries to curie amounts, of very high specific activity labeled compounds. Specifically, use of a substantially carrier-free metallo tritide, such as substantially carrier-free lithium aluminum tritide (LiAl³H₄), yields a ditritium-labeled alcohol II with essentially 100% tritide atoms. As this alcohol II is further oxidized to aldehyde III, which is further condensed to ester IV, each step in the process maintains essentially pure tritide substitution at carbon 11, leading to final tritium-labeled products with very high specific activity of preferably at least 15 Ci/mmol, more preferably at least 25 Ci/mmol. These high specific activity monotritium-labeled 9-cis retinoids will in turn prove very useful in ligand binding assays, metabolism studies and ³HNMR studies. In contrast, typical radiolabeling methods, such as those found in Kaegi et al., supra, reduce an aldehyde with a typically impure tritium reducing agent. Thus, the alcohol intermediate at best contains one tritide and one hydride atom, and more typically is also mixed with alcohol molecules containing only hydride substitutions. When carded through its final synthesis steps, such methodologies yield low amounts of low activity labeled retinoids, typically with a specific activity of 3 Ci/mmol, or less. In this regard, these low activity materials are not useful for ligand binding or proton NMR studies, as such materials are not readily detectable at the sensitivity level of such studies, i.e. the readings obtained from such materials cannot be distinguished from background radioactivity levels.

In a second aspect, the present invention also provides methods of discovering retinoid X receptor (RXR) active and specific ligands. In particular, a radiolabeled compound which is capable of binding to a RXR, such as a monotritium-labeled 9-cis retinoid made by any of the methods of the present invention, can be used in a competition binding assay against the ligand to be tested. By comparing the degree to which the tritium-labeled compound and ligand bind to the RXR relative to the degree of binding of the tritium-labeled compound to the RXR in the absence of the ligand, the activity of the ligand on the RXR can be determined.

The variations in conducting such competition binding assays are well known to those skilled in the art. For example, one method of conducting such an assay is to first incubate the tritium-labeled compound in a medium containing an RXR protein until the tritium-labeled compound is bound to the RXR protein to the point of saturation. Thereafter, the bound RXR protein is washed and incubated with a high concentration (e.g. 200 times) of the ligand (e.g., non-labeled 9-cis retinoic acid) to be tested. By comparing the quantity of bound tritium-labeled compound displaced by the ligand the relative activity of the ligand on the RXR, if any, can be determined. Alternatively, when the saturation curve of the tritium-labeled compound on the RXR is already known, then the tritium-labeled compound and ligand can be incubated with the RXR at the same time, and the degree of exclusion of the binding of the tritium-labeled compound to the RXR used to measure the relative activity of the ligand on the RXR, if any.

The RXR proteins used in the competition binding assays of the methods of the present invention will generally be recovered from cell lysates of an appropriate cell culture transfected with a recombinant plasmid capable of expressing the RXR proteins. However, any appropriate means of expressing a sufficient quantity of one or more retinoid X receptors to allow for the conducting of the identification methods of the present invention can be employed. Furthermore, any biologically compatible medium in which the competition binding assays of the present invention can function is considered to be within the scope of the present invention.

To help ensure an accurate measurement of the amount of tritium-labeled compound that can bind to a particular RXR, it is preferred that the specific binding of the tritium-labeled compound be determined by titrating the bound tritium-labeled compound against an excess quantity of the same compound in a nonradioactive form. For example, the tritium-labeled compound is first incubated with a given RXR to the point of saturated binding. An appropriate binding curve is then generated which shows total binding, both specific binding to the RXR pocket, and nonspecific binding to other associated structures (e.g. lipids). Thereafter, the RXR bound with the tritium-labeled compound is incubated with a large excess of the nonradioactive version of the tritium-labeled compound (e.g. 200 times or greater concentration). Any tritium-labeled compound that remains bound, as shown by an appropriate binding curve, is nonspecifically bound. By subtracting the nonspecifically bound protein from the total bound protein, a bending curve can be generated which shows the total specific binding of the tritium-labeled compound to the RXR. This in turn provides the reference useful for determining the concentration of a tested ligand that displaces the tritiumlabeled compound from an RXR in the methods of the present invention.

In a preferred aspect of the method of the present invention, the tritium-labeled compound will show activity (e.g. binding) on both retinoid X receptors (RXRs) and retinoic acid receptors (RARs). In such an instance, the tritium-labeled compound can be used to not only identify compounds that are active on RXRs and RARs, but will also prove useful for identifying ligands that selectively activate one subfamily of retinoid receptors, but not the other. For example, such a tritium-labeled compound would prove useful for identifying ligands that selectively activate one or more RXR, but do not activate any of the RARs. In fact, such a preferred compound is monotritium-labeled 9-cis retinoic acid (9-cis RA) and its related analogs formed via the methods of the present invention. As can be seen in Table 1 herein, 9-cis RA is active on all six known retinoid receptors (RARα,β,γ and RXRα,β,γ), in contrast to all-trans retinoic acid (ATRA), which is only active on RARα,β,γ. Thus, 9-cis RA can be used in the method of the present invention to identify ligands which are specific to any one of the six retinoid receptors, in addition to identifying ligands that are specific to either the RAR or RXR subfamily of receptors.

The invention will be further illustrated by reference to the following non-limiting Examples.

EXAMPLE 1

Syntheses of retinoids according to the present invention were performed using both lithium aluminum hydride, thereby yielding nonradioactive retinoids, and substantially carrier-free lithium aluminum tritide, yielding high activity 9-cis monotritium-labeled retinoids. The synthesis is presented for the nonradioactive retinoids, including all the necessary physical and spectral properties, to provide a means of characterizing the radioactive (monotritium-labeled) intermediates and final monotritium-labeled 9-cis retinoid products.

Synthesis of nonradioactive 9-cis retinoic acid (V)

The synthesis of nonradioactive retinoids utilized the same methodology as that illustrated for the synthesis of the 9-cis monotritium-labeled retinoids disclosed and claimed herein. Accordingly, reference numerals will be inserted corresponding with those used in the illustration of the synthesis of 9-cis monotritium-labeled retinoids. However, it is to be understood that the nonradioactive synthesis utilized lithium aluminum hydride (LiAlH$_4$) versus the substantially carrier-free lithium aluminum tritide (LiAl$^3$H$_4$) used in the synthesis of the monotritium-labeled 9-cis retinoids.

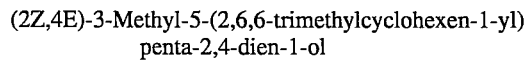
(2Z,4E)-3-Methyl-5-(2,6,6-trimethylcyclohexen-1-yl) penta-2,4-dien-1-ol (II, where R$^1$, R$^2$, R$^3$ and R$^4$ are methyl) To 40 mg (0.16 mmol) of methyl (2Z,4E)-3 -methyl-5-(2,6,6-trimethylcyclohex-1-enyl)penta-2,4-dienoate I in 2 mL of anhydrous tetrahydrofuran (THF) at −78° C. was added (0.25 mmol) of LiAlH$_4$. The reaction was stirred at −78° C. for 15 min and warmed to room temperature (RT). When the reaction was complete, as monitored by thin-layer chromatography (TLC), 2 mL of H$_2$O was added and the organics extracted with ether and washed 3 X with 5 mL of water. The organic layer was dried with MgSO$_4$, filtered, concentrated in vacuo and the dienol II was used directly in the next step. TLC (20% EtOAc-hexane) R$_f$ 0.26 (cis isomer), $^1$H-NMR δ1.01 (s, (CH$_3$)$_2$), 1.46 (t, J=6 Hz, CH$_2$ ), 1.62 (dr, J= 6 Hz, J=4 Hz, CH$_2$), 1.70 (s, CH$_3$, 1.91 (s, CH$_3$), 2.01 (t, J=6 Hz, CH$_2$), 4.30 (d, J=6 Hz, CH$_2$ ), 5.54(t,J= 6 Hz, CH), 6.19 (d, J=16 Hz, CH), 6.39 (d, J=16 Hz, CH).

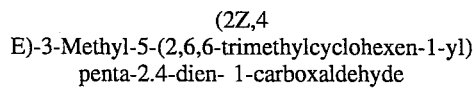
(2Z,4 E)-3-Methyl-5-(2,6,6-trimethylcyclohexen-1-yl) penta-2.4-dien- 1-carboxaldehyde (III, where R$^1$, R$^2$, R$^3$ and R$^4$ are methyl) To the crude dienol II in 5 mL of CH$_2$Cl$_2$ was added 100 mg (1.1 mmol) of MnO$_2$. The reaction was stirred vigorously for 1 hr at RT or until complete by TLC. The product has a distinct yellow/brown color upon heating a vanillin stained TLC plate. Two products were observed by TLC and were identified as 2E:4Z and 2E:4E isomers in approximately a 5:1 ratio by $^1$H-NMR. After completion, the reaction mixture was filtered through celite, and the celite was washed with $CH_2Cl_2$ (3×15 mL). The filtrate was concentrated to provide aldehyde III, which was used directly in the next step. TLC (20% EtOAc-hexane) $R_f$ 0.55 (cis), 0.47 (trans). $^1$H-NMR δ (CDCl$_3$) (cis isomer)1.06 (s, (CH$_3$)$_2$), 1.50 (t, J= 2 Hz, CH$_2$)), 1.63 (dt, J=6 Hz, J=2 Hz, CH$_2$), 1.75 (s, CH$_3$), 2.06 (t, J=6 Hz, CH$_2$ ), 2.13 (s, CH$_3$), 5.87 (d, J=8 Hz, CH), 6.63 (d, J=16 Hz, CH), 7.09 (d, J=16 Hz, CH), 10.17 (d, J= 8 Hz, CH).

Ethyl (2E,4E,6Z,8E)-3,7-dimethyl-9(2,6,6-trimethylcyclohexen-1 -yl)nona-2,4,6,8 -tetraenoate (IV, where $R^1$, $R^2$, $R^3$, $R^4$ and $R^6$ are methyl, and $R^7$ is ethyl) (ethyl 9-cis retinoate). To 40 mg (0.15 mmol) of the phosphonate (diethyl 3-ethoxycarbonyl-2 -methylprop-2-enylphosphonate) in 3 mL of dry THF was added 7 mg (0.18 mmol) of sodium hydride (60% wt in oil). The reaction was stirred at RT for 0.5 hr, cooled to 0° C, followed by addition of aldehyde III in 2 mL of THF. The reaction was warmed to RT and stirred for an additional 30 minutes, followed by addition of 3 mL of H$_2$O. The organic layer was extracted with ether (3×5mL), dried (MgSO$_4$), filtered, concentrated in vacuo to afford crude ester IV, which was used directly in the next step. TLC (20% EtOAc-hexane) $R_f$ 0.79, $^1$H-NMR δ (CDCl$_3$) (cis isomer)1.04 (s, (CH$_3$)$_2$), 1.27 (t, J=8 Hz, CH$_2$CH$_3$), 1.48 (t, J=3 Hz, CH$_2$), 1.64 (tt, J=6 Hz, J=3 Hz, CH$_2$), 1.75 (s, CH$_3$), 2.01 (S, CH$_3$), 2.05 (t, J=6 Hz, CH$_2$), 2.352 (s, CH$_3$), 4.15 (q, J= 8 Hz, CH$_2$CH$_3$), 5.78 (s, CH), 6.05 (d, J=11.5 Hz, CH or CH), 6.25 (d, J=15 Hz, CH or CH), 6.29 (d, J=16.8 Hz, CH), 6.62 (d, J=16 Hz, CH), 7.06 (dd, J=11.5 Hz, J=15 Hz, CH).

(2E,4E,6Z,8E)-3.7-Dimethyl-9-(2,6,6-trimethylcyclohexen-1-yl)nona-2.4.6.8-tetraenoic acid (V, where $R^1$, $R^2$, $R^3$, $R^4$ and $R^6$ are methyl, and $R^8$ is hydrogen) (9-cis retinoic acid). To ester IV in 5 mL of MeOH was added 0.5 mL of 5N KOH and the reaction heated to 60° C. for 1 hr. After the hydrolysis was complete (by TLC) the solution was cooled to 0° C. and acidified with 1N HCl. The mixture was extracted with ether (3×10 mL), dried over MgSO$_4$, and concentrated in vacuo to give the crude acid. The product was purified by crystallization from MeOH to give 8 mg (0.027 mmol) of pure 9-cis retinoic acid V (17 % overall yield from methyl ester I). TLC (20% EtOAc-hexane) $R_f$ 0.26; mp=189° C. (M. F. Boehm et al., *J. Med. Chem.*, 37:408–414 (1994): (187°–189° C.); UV (MeOH) $\lambda_{max}$ 343 nm (ε=39,000); $^1$H-NMR, δ (CDCl$_3$) (cis isomer)1.04 (s, (CH$_3$)$_2$), 1.49 (t, J=3 Hz, CH$_2$), 1.64 (it, J= 6 Hz,J=3 Hz,CH$_2$), 1.75 (s,CH$_3$), 2.01 (s,CH$_3$), 2.05 (t, J=6 Hz, CH$_2$), 2.35 (s, CH$_3$), 5.80 (s, CH), 6.06 (d, J=11.5 Hz, CH), 6.25 (d, J=15 Hz, CH), 6.29 (d, J=16 Hz, CH), 6.65 (d, J=16 Hz, CH), 7.13 (dd, J=11.5 Hz, J=15 Hz, CH), $^1$H-NMR (CD$_3$OD) δ1.05 (s, (CH$_3$)$_2$), 1.52 (t, J=3 Hz, CH$_2$), 1.65 (tt, J=6 Hz, J=3 Hz, CH$_2$), 1.75 (s, CH$_3$), 2.00 (s, CH$_3$), 2.06 (t, J=6 Hz, CH$_2$), 5.79 (s, CH), 6.11 (d, J=12 Hz, CH), 6.30 (brd, J= 17Hz+J=15Hz, CH+CH),6.70(d,J=17Hz, CH),7.11 (dd, J= 11.5Hz+J= 15.1 Hz, CH). MS (FAB+: calculated for CHO>300.20892) found=300.20867, calcd=300.20892.

Synthesis of $^3$H-9-cis retinoic acid (V)

(2Z,4E)-1,1-[$^3$H]-3-Methyl-5-(2,6,6-trimethylcyclohexen-1-yl)penta-2,4 -dien-1-ol (II, where $R^1$, $R^2$, $R^3$ and $R^4$ are methyl) To (0.25 mmol) of LiAl$^3$H$_4$ in 1 mL of tetrahydrofuran (THF) at −78° C. was added 40 mg (0.16 retool) of methyl ester I in 2 mL of anhydrous THF. The reaction was stirred at −78° C. for 15 min. and warmed to room temperature (RT) for 6 hours. When the reaction was approximately 40% complete, as monitored by thin-layer chromatography (TLC), 2 mL of MeOH was added and the volatile components removed in vacuo. The organics were resuspended in ether and washed 3X with 5 mL of water. The organic layer was dried with MgSO$_4$, filtered, and concentrated in vacuo to give alcohol II, which was used directly in the next step. TLC (20% EtOAc-hexane) $R_f$ 0.26 (cis), 0.20 (trans).

(2Z,4E)-1-[$^3$H]-3-Methyl-5-(2,6,6-trimethylcyclohexen-1-yl)penta-2.4 -dien-1carboxaldehyde (III, where $R^1$, $R^2$, $R^3$ and $R^4$ are methyl) To the crude alcohol II in 5 mL of CH$_2$Cl$_2$ was added 100 mg (1.1 mmol) of MnO$_2$. The reaction was stirred vigorously at RT until complete by TLC. The product had a distinct yellow/brown color upon heating a vanillin stained TLC plate. Two products in approximately a 1:1 ratio were observed by TLC and were identified as trans (E:E) and cis (E:Z) configuration. After the oxidation reaction was complete (by TLC), the product was filtered through celite, and the celite was washed 3 X with CH$_2$Cl$_2$. The filtrate was concentrated to give crude aldehyde III, which was used directly in the next step. TLC (20% EtOAc-hexane) $R_f$ 0.55 (cis), 0.47 (trans).

Ethyl (2E,4E,6Z,8E)-5-[$^3$H]-3,7-dimethyl-9-(2.6.6-trimethylcyclohexen-1-yl)nona-2,4,6,8-tetraenoate (IV, where $R^1$, $R^2$, $R^3$, $R^4$ and $R^6$ are methyl, and $R^7$ is ethyl) Ethyl (11-[$^3$H]-9-cis retinoate). To 40 mg (0.15 mmol) of the phosphonate (diethyl 3 -ethoxycarbonyl-2-methylprop-2-enylphosphonate) in 3 mL of dry THF was added 7 mg (0.18 mmol) of 60% in oil sodium hydride. The reaction was stirred at RT for 0.5 hr, cooled to 0° C., followed by addition of aldehyde III in 2 mL of THF. The reaction was warmed to room temperature and stirred for an additional 30 min. Water (3 mL) was added, and the organic layer was extracted with ether (3×5mL), dried over MgSO$_4$, filtered, concentrated (rotoevaporator), and the crude ester IV used directly in the next step. TLC (20% EtOAc-hexane) $R_f$ 0.79.

(2E,4E,6Z,8E)-5-[$^3$H]-3,7-Dimethyl-9-(2,6,6-trimethylcyclohexen-1 -yl)nona-2,4,6,8-tetraenoic acid (V, where $R^1$, $R^2$, $R^3$, $R^4$ and $R^6$ are methyl, and $R^8$ is hydrogen) (11-[ $^3$H]-9-cis retinoic acid). To ester IV in 5 mL of MeOH was added 0.5 mL of 5N KOH and the reaction was heated to 60° C. for 1 hr. After hydrolysis was complete (by TLC) the solution was cooled to 0° C. and acidified with 1N HCl. The organic layer was extracted with ether (3×10 mL), dried over MgSO$_4$, and concentrated in vacuo. The product acid V was purified by ODS HPLC to give 110 mCi of 9-cis retinoic acid and 80 mCi of all-trans retinoic acid. The specific activity was approximately 29 Ci/mmol and was determined by $^3$H-NMR and $^1$H-NMR which showed only tritium and no detectable hydrogen at the 11 position of 9-cis and all-trans retinoic acids. TLC (20% EtOAc-hexane) $R_f$ 0.26, UV(MeOH) $\lambda_{max}$ 343 nm; $^1$H-NMR (CD$_3$OD) δ 1.05 (s, (CH$_3$)$_2$), 1.52 (t, J=3 Hz, CH$_2$), 1.65 (tt, J=6 Hz, J=3 Hz, CH$_2$), 1.75 (s, CH$_3$), 2.00 (s, CH$_3$), 2.06 (t, J=6 Hz, CH$_2$), 5.79 (s, CH), 6.11 (d, J=12 Hz, CH), 6.30 (brd, J= 17Hz+J=15Hz, CH+CH),6.70(d,J=17Hz, CH),7.11 (dd, J=11.5Hz+J= 15.1 Hz, CH). $^3$H-NMR (CD$_3$OD) δ7.11 (dd, J=12.1 Hz+J=15.7 Hz, C$^3$H).

EXAMPLE 2

For binding studies, retinoids receptors were used employing a baculovirus expression system. The methods concerning growth, purification, and assays of recombinant viruses followed the protocol outlined by Summers, M. D., and Smith, G. E., *A Manual of Methods for Baculovirus Vectors and Insect Cell Culture Procedures, Texas Agric. Exp. Stat. Bull.*, No. 155 (1987), the disclosure of which is herein incorporated by reference. The recombinant plasmids were cotransfected into SF21 cells with wild-type AcNPV DNA, See U.S. Pat. No. 5,071,773, and the recombinant viruses were plaque purified. For the mock (control) extracts, wild-type AcNPV-infected cells were used.

For ligand binding assays, the baculovirus-infected cells were disrupted by Dounce homogenization (Kontes Co., Vineland, N.J.) in 10 nM Tris (pH 7.6), 5 mM dithiothreitol (DTT), 2 mM EDTA 0.5% CHAPS, and 1 mM phenylm-ethyisulfonyl fluoride. The KCl concentration was adjusted to 0.4M after cell lysis. The cell lysates were centrifuged for 1 hr at 4° C., 100,000× g, and the supernatant was recovered as a high-salt, whole cell extract. For the saturation binding analysis, cell extracts (50 microgram protein) were incubated at 0° C. for 2.0 hr with a 11-$^3$H-labeled retinoid in the presence or absence of 200-fold excess unlabeled ligand. Specific ligand binding to receptor was determined by a hydroxyapatite binding assay according to the protocol of Wecksler, W. R., and Norman, A. W., *Anal. Biochem.*, 92:314–323 (1979).

Figure 1B:
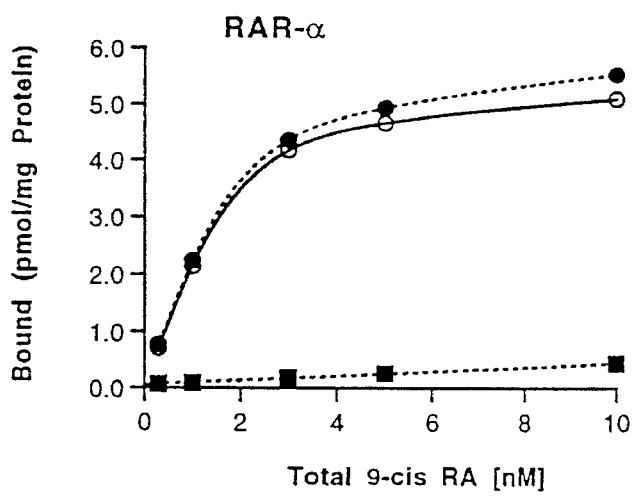
FIG. 1B is a graph showing the total binding ●, nonspecific binding ■, and total specific binding ○ of monotritium-labeled 9-cis retinoic acid (11-[$^3$H]-9-cis retinoic acid) to RARα at increasing concentrations of 9-cis retinoic acid.
Figure 1C:
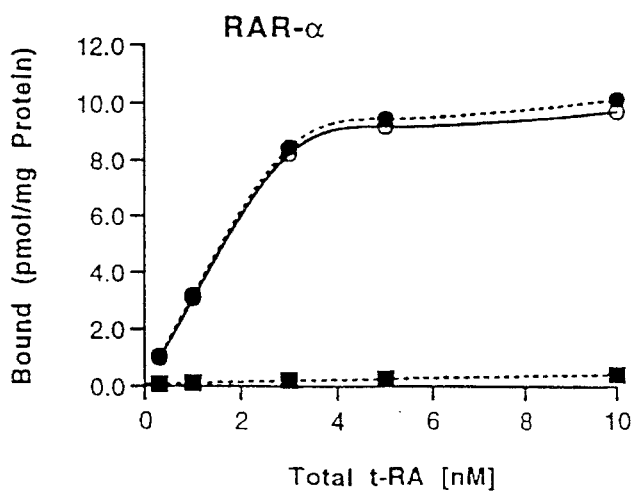
FIG. 1C is a graph showing the total binding ●, nonspecific binding ■, and total specific binding ○ of monotritium-labeled all-trans retinoic acid ( 11-[$^3$H] -all-trans retinoic acid) to RXRα at increasing concentrations of all-trans retinoic acid.

To characterize the binding of 9-cis retinoic acid to baculovirus-derived RARs and RXRs, saturation binding analysis were performed using 11-[$^3$H]-9-cis retinoic acid. A typical binding curve for 9-cis retinoic acid binding to RARα and RXR α is shown in FIGS. 1A and 1B. A comparable curve for all-trans retinoic acid binding to RARα is shown in FIG. 1C. Since all-trans retinoic acid does not bind to RXRs, no figure is shown for all-trans retinoic acid binding to RXRα.

In FIGS. 1A–C, the curves represented by ● are lysate incubated with 11-[$^3$H]-9-cis retinoic acid alone, which shows the total of specific and nonspecific binding. Non-specific binding is shown with the curves represented by ■, and was determined by adding 1 nM of 11-[$^3$H]-9-cis retinoic acid together with 200 nM of 9 cis retinoic acid, effectively competing off the specifically bound 11-[$^3$H]-9-cis retinoic acid with the non-labeled 9-cis retinoic acid. Any remaining non-bound 11-[$^3$H]-9-cis retinoic acid is due to nonspecific binding. Specific binding is determined by subtracting the values for nonspecifically bound 11-[$^3$H]-9-cis retinoic acid from total bound 11-[$^3$H]-9-cis retinoic acid, and is represented by the curve ○. Scatchard analysis of the binding of 11-[$^3$H]-9-cis retinoic acid and 11-[$^3$H]-all-trans retinoic acid to RARα,β,γ and RXRα, β,γ gave the dissociation constants shown in Table 1 below. The data shows that 9-cis retinoic acid effectively binds to all six receptors whereas all-trans retinoic acid only binds to the RARs. We conclude that 9-cis retinoic acid binds to the RARs and RXRs with high affinity in a saturable and specific manner.

TABLE 1

Mean dissociation constants in Kd (nM) (and standard deviation) for RAR and RXR retinoid receptors with all-trans retinoic acid (ATRA) and 9-cis retinoic acid (9-cis RA).

| Retinoid | RARα | RARβ | RARγ | RXRα | RXRβ | RXRγ |
|---|---|---|---|---|---|---|
| ATRA Mean | 0.45 | 0.37 | 0.22 | — | — | — |
| s.d. | 0.13 | 0.13 | 0.11 | — | — | — |
| 9-cis RA Mean | 0.32 | 0.20 | 0.78 | 1.38 | 2.11 | 1.94 |
| s.d. | 0.07 | 0.09 | 0.14 | 0.37 | 0.75 | 0.76 |

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A method for producing a 9-cis monotritium-labeled retinoid comprising:

(a) reducing an alkyl ester of the formula:

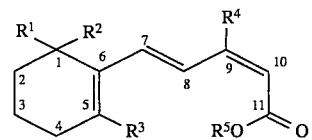

with a substantially carrier-free metallo tritide selected from the group consisting of substantially carrier-free lithium aluminum tritide and substantially carrier-free lithium triethyl aluminum tritide to form a ditritium alcohol of the formula:

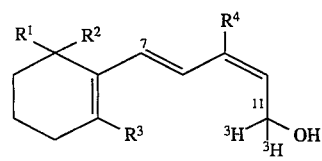

(b) oxidizing the ditritium alcohol to a monotritium aldehyde in the presence of an oxidizing agent;

(c) condensing the monotritum aldehyde with a carbanion equivalent formed by the addition of a base to a phosphonate or phosphine salt of the formula:

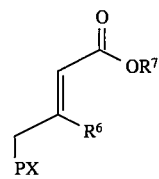

to form a reaction product comprising a mixture of 9-cis monotritium-labeled retinoid ester stereoisomers having the general formula:

13

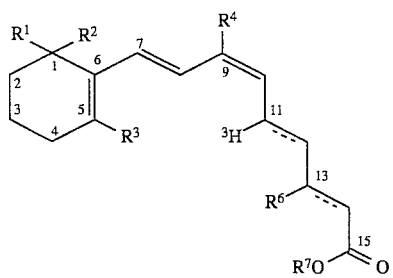

wherein $R^1$, $R^2$ and $R^3$ each independently represent hydrogen or a lower straight chain or branched alkyl having 1–6 carbon atoms; $R^4$ represents hydrogen or a lower straight chain or branched alkyl having 1–12 carbon atoms; $R^5$ represents a lower alkyl having 1–5 carbon atoms; $R^6$ represents hydrogen or a lower straight chain or branched alkyl having 1–12 carbon atoms; $R^7$ represents a lower alkyl having 1–5 carbon atoms; $R^8$ represents hydrogen or a pharmaceutically acceptable salt; PX represents dialkyl phosphonate or a triphenyl phosphine salt; and the dashed lines in the structures between carbons 11–12 and 13–14 depict olefin bonds that can be in either the trans or cis configuration and further wherein, said 9-cis monotritium-labeled retinoid ester steroisomers display a specific activity of at least 15 Curries per millimole.

2. The method of claim 1, further comprising, after the condensing step, hydrolyzing the reaction product with an aqueous methanolic hydroxide to form a mixture of 9-cis monotritium-labeled retinoid stereoisomers.

3. The method of claim 2, further comprising, after the hydrolyzing step, isolating a 9-cis monotritium-labeled retinoid stereoisomer having the general formula

14

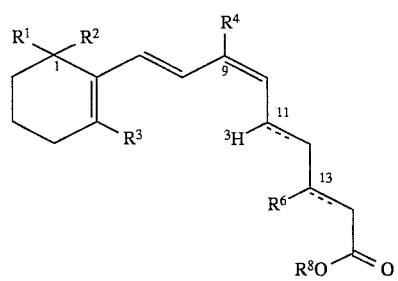

wherein $R^1$, $R^2$, $R^3$, $R^4$, $R^5$, $R^6$ and $R^8$ have the meaning specified above, and wherein the 11–12 and 13–14 olefin bonds are in either the trans or cis configuration.

4. The method of claim 1, wherein the base is selected from the group consisting of sodium hydride, potassium hydride, n-butyl lithium, s-butyl lithium, t-butyl lithium, and sodium amide.

5. The method of claim 3, wherein the 9-cis monotritium-labeled retinoid stereoisomer comprises (2E,4E,6Z,8E)-5-[$^3$H]-3,7-dimethyl-9-(2,6,6 -trimethylcyclohexen-1-yl)nona-2,4,6,8-tetraenoic acid, (2E,4Z,6Z, 8E)-5-[$^3$H]-3,7 -dimethyl-9-(2,6,6-trimethylcyclohexen-1-yl)nona-2,4,6,8-tetraenoic acid, or (2Z,4E,6Z, 8E)-5-[$^3$H]-3,7-dimethyl-9-(2,6,6-trimethylcyclohexen- 1-yl)nona-2,4,6,8-tetraenoic acid.

6. The method of claim 1, wherein the 9-cis monotritium-labeled retinoid ester stereoisomers display a specific activity of at least 25 Curies per millimole.

7. A monotritium-labeled 9-cis retinoid made according to the method of claim 1.

8. A monotritium-labeled 9-cis retinoid according to claim 7 selected from the group consisting of (2E,4E,6Z,8E)-5-[$^3$H]-3,7-dimethyl-9-( 2,6,6-trimethylcyclohexen- 1-yl) nona-2,4,6,8-tetraenoic acid, (2E,4Z,6Z, 8E)-5-[$^3$H]-3,7-dimethyl-9-( 2,6,6-trimethylcyclohexen-1-yl)nona-2,4,6,8-tetraenoic acid and (2Z,4E,6Z, 8E)-5-[ $^3$H]-3,7-dimethyl-9-(2,6,6-trimethylcyclohexen-1-yl)nona-2,4,6,8-tetraenoic acid.

* * * * *